US009849004B2

(12) United States Patent
Choi et al.

(10) Patent No.: US 9,849,004 B2
(45) Date of Patent: Dec. 26, 2017

(54) WEARABLE ROBOT AND METHOD OF CONTROLLING THE SAME

(71) Applicant: Samsung Electronics Co., Ltd., Suwon-Si, Gyeonggi-Do (KR)

(72) Inventors: Jong Do Choi, Suwon-si (KR); Young Do Kwon, Yongin-si (KR); Gyung Rock Kim, Yongin-si (KR); Ji Min Kim, Seoul (KR); Young Bo Shim, Seoul (KR); Tae Sin Ha, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 265 days.

(21) Appl. No.: 14/476,342

(22) Filed: Sep. 3, 2014

(65) Prior Publication Data
US 2015/0119996 A1 Apr. 30, 2015

(30) Foreign Application Priority Data
Oct. 31, 2013 (KR) .......................... 10-2013-0130953

(51) Int. Cl.
*A61F 2/68* (2006.01)
*A61H 3/00* (2006.01)
*A61F 5/01* (2006.01)

(52) U.S. Cl.
CPC .................. *A61F 2/68* (2013.01); *A61F 5/01* (2013.01); *A61H 3/00* (2013.01); *A61H 2201/5061* (2013.01); *A61H 2201/5069* (2013.01)

(58) Field of Classification Search
CPC .... B25J 9/0006; A61H 3/00; A61H 2009/001; A61H 1/0262; A61B 5/04888; A61B 5/112; A61B 5/1121; A61B 5/1123; A61B 5/1038
See application file for complete search history.

(56) References Cited

U.S. PATENT DOCUMENTS

| | | | | |
|---|---|---|---|---|
| 6,402,635 | B1 * | 6/2002 | Nesbit ................ | A63B 69/3667 473/131 |
| 6,500,138 | B1 * | 12/2002 | Irby ...................... | A61F 5/0125 602/26 |
| 7,447,593 | B2 * | 11/2008 | Estkowski ............. | G01C 21/20 700/250 |
| 7,643,903 | B2 * | 1/2010 | Kawai .................. | B62D 57/032 318/568.1 |
| 2004/0167641 | A1 * | 8/2004 | Kawai .................. | A61B 5/1038 700/63 |

(Continued)

FOREIGN PATENT DOCUMENTS

| JP | 2005230099 A | 9/2005 |
|---|---|---|
| JP | 2011147556 A | 8/2011 |

(Continued)

*Primary Examiner* — Justine Yu
*Assistant Examiner* — Christopher Miller
(74) *Attorney, Agent, or Firm* — Harness, Dickey & Pierce, P.L.C.

(57) ABSTRACT

Provided is a method of controlling a wearable robot, the method including: measuring a ground reaction force (GRF) exerted on a wearer's soles; calculating a time variation rate of the measured GRF; measuring the wearer's knee joint angle; and detecting a time point at which the calculated time variation rate of the GRF and the measured knee joint angle cross each other.

15 Claims, 10 Drawing Sheets

(56) References Cited

U.S. PATENT DOCUMENTS

| | | | |
|---|---|---|---|
| 2005/0119791 A1* | 6/2005 | Nagashima | B25J 9/161 700/253 |
| 2006/0122710 A1* | 6/2006 | Bedard | A61F 2/644 623/24 |
| 2006/0149420 A1* | 7/2006 | Ikeuchi | B62D 57/032 700/245 |
| 2006/0211956 A1* | 9/2006 | Sankai | A61B 5/04888 601/5 |
| 2008/0009771 A1* | 1/2008 | Perry | B25J 9/0006 600/587 |
| 2008/0039756 A1* | 2/2008 | Thorsteinsson | A61B 5/1038 602/23 |
| 2008/0133057 A1* | 6/2008 | Hasegawa | B62D 57/032 700/258 |
| 2008/0161937 A1* | 7/2008 | Sankai | A61H 3/008 623/25 |
| 2008/0234608 A1* | 9/2008 | Sankai | A61B 5/04888 601/5 |
| 2009/0319054 A1 | 12/2009 | Sankai | |
| 2010/0076360 A1* | 3/2010 | Shimada | A61B 6/037 602/23 |
| 2010/0094188 A1* | 4/2010 | Goffer | B25J 9/0006 602/23 |
| 2010/0113980 A1* | 5/2010 | Herr | A61F 2/60 600/587 |
| 2010/0114329 A1* | 5/2010 | Casler | B25J 19/0008 623/24 |
| 2010/0324699 A1* | 12/2010 | Herr | A61F 2/66 623/27 |
| 2011/0082566 A1* | 4/2011 | Herr | A61F 2/60 623/24 |
| 2013/0006159 A1* | 1/2013 | Nakashima | A61H 1/024 602/23 |
| 2014/0128778 A1* | 5/2014 | Chan | A61B 5/1116 600/595 |
| 2015/0025423 A1* | 1/2015 | Caires | A61H 1/024 601/35 |

FOREIGN PATENT DOCUMENTS

| | | |
|---|---|---|
| JP | 2012040113 A | 3/2012 |
| KR | 20120107928 A | 10/2012 |

\* cited by examiner

WEARABLE ROBOT AND METHOD OF CONTROLLING THE SAME

CROSS-REFERENCE TO RELATED APPLICATION

This application claims the benefit of Korean Patent Application No. P2013-130953, filed on Oct. 31, 2013 in the Korean Intellectual Property Office, the disclosure of which is incorporated herein by reference.

BACKGROUND

1. Field

Example embodiments relate to a wearable robot and a method of controlling the same. In one or more example embodiments, the wearable robot is configured to detect a standing time point and generate an auxiliary torque for assisting muscle strength.

2. Description of the Related Art

Wearable robots having various purposes, such as for helping movements of disabled persons, the elderly, and the infirm by assisting their muscle strengths when they move, for rehabilitation treatment for muscle disease patients, for soldiers who carry heavy military gears, or for industrial sites in which workers carry heavy loads have been briskly developed.

Wearable robots used for soldiers or industrial sites may generate relatively larger forces than the forces generated by an ordinary human being, whereas wearable robots used for the disabled person or the elderly and infirm may generate relatively smaller forces to assist the wearer with day-to-day activities. Wearable robots used for the disabled, elderly and infirm persons help the wearer to have a convenient life, and may be classified as part of smart aging technologies, which has been receiving attention in light of an aging society.

Walking assisting apparatuses may improve the quality of life by improving a moving ability that is a basic, essential life element for the human being. That is, when elderly people who cannot walk for a long time wear the walking assisting apparatuses, they can experience various activities that they would not otherwise be able to partake in, and can be more active and thus, the walking assisting apparatuses can be used for rehabilitation. Also, the walking assisting apparatuses may serve as wearable computers and thus can be used for real-time health check and assist in an emergency situation through combined various information technologies.

These walking assisting apparatuses can be classified into several types, such as exoskeleton type walking assisting apparatuses in which frames are mounted on all of hips, knees, and ankles, or walking assisting apparatuses that are worn only on a waist and thighs so as to assist only the hip joint, according to purposes.

Also, since a walking assisting apparatus is based on movement, batteries may be mounted on the walking assisting apparatus, and the walking assisting apparatus may be light-weight to not burden the wearer. When assisting the wearer, it may be desirable to have the walking assisting apparatus generate an optimum joint torque at an exact time point.

SUMMARY

Example embodiments are directed to a wearable robot generates an auxiliary torque at which a wearer does not feel resistance, at an appropriate time point, and a method of controlling the wearable robot.

Additional aspects of the example embodiments will be set forth in part in the description which follows and, in part, will be obvious from the description, or may be learned by practice of the example embodiments.

Some example embodiments relate to a method of controlling a wearable robot.

In some example embodiments, the method includes measuring a ground reaction force (GRF) exerted on a wearer's soles and the wearer's knee joint angle; detecting a time point at which a graph of a time variation rate of the GRF and a graph of the knee joint angle cross each other; and determining the detected crossing time point as a time point at which the wearer starts a standing movement and applying an auxiliary torque to the wearable robot from the time point.

In some example embodiments, the method includes determining a time point at which a wearer starts a standing movement; generating an auxiliary torque having a trigonometrical function wave shape in which a plurality of sinusoidal waves overlap each other; and applying the generated auxiliary torque to the wearable robot from the determined time point.

Some example embodiments relate to a wearable robot.

In some example embodiments, the wearable robot includes: a robot unit configured as an instrument for assisting a wearer's muscle strength; a ground reaction force (GRF) measuring portion measuring a GRF exerted on the wearer's soles; a joint angle measuring portion measuring the wearer's knee joint angle and the wearer's hip joint angle; and a controller detecting a time point at which a graph of a time variation rate of the GRF measured using the GRF measuring portion and a graph of the knee joint angle cross each other, determining the detected time point as a time point at which the wearer starts a standing movement, and applying an auxiliary torque to the robot unit from the determined time point.

In some example embodiments, the wearable robot includes: a robot unit configured as an instrument for assisting a wearer's muscle strength; a joint angle measuring portion measuring the wearer's knee joint angle and the wearer's hip joint angle; and a controller determining a time point at which the wearer starts a standing movement, generating an auxiliary torque having a trigonometrical function wave shape in which a plurality of sinusoidal waves overlap each other, and then applying the generated auxiliary torque to the robot unit from the determined time point.

BRIEF DESCRIPTION OF THE DRAWINGS

These and/or other aspects of the example embodiments will become apparent and more readily appreciated from the following description of some of the example embodiments, taken in conjunction with the accompanying drawings of which.

DETAILED DESCRIPTION

Figure 1:
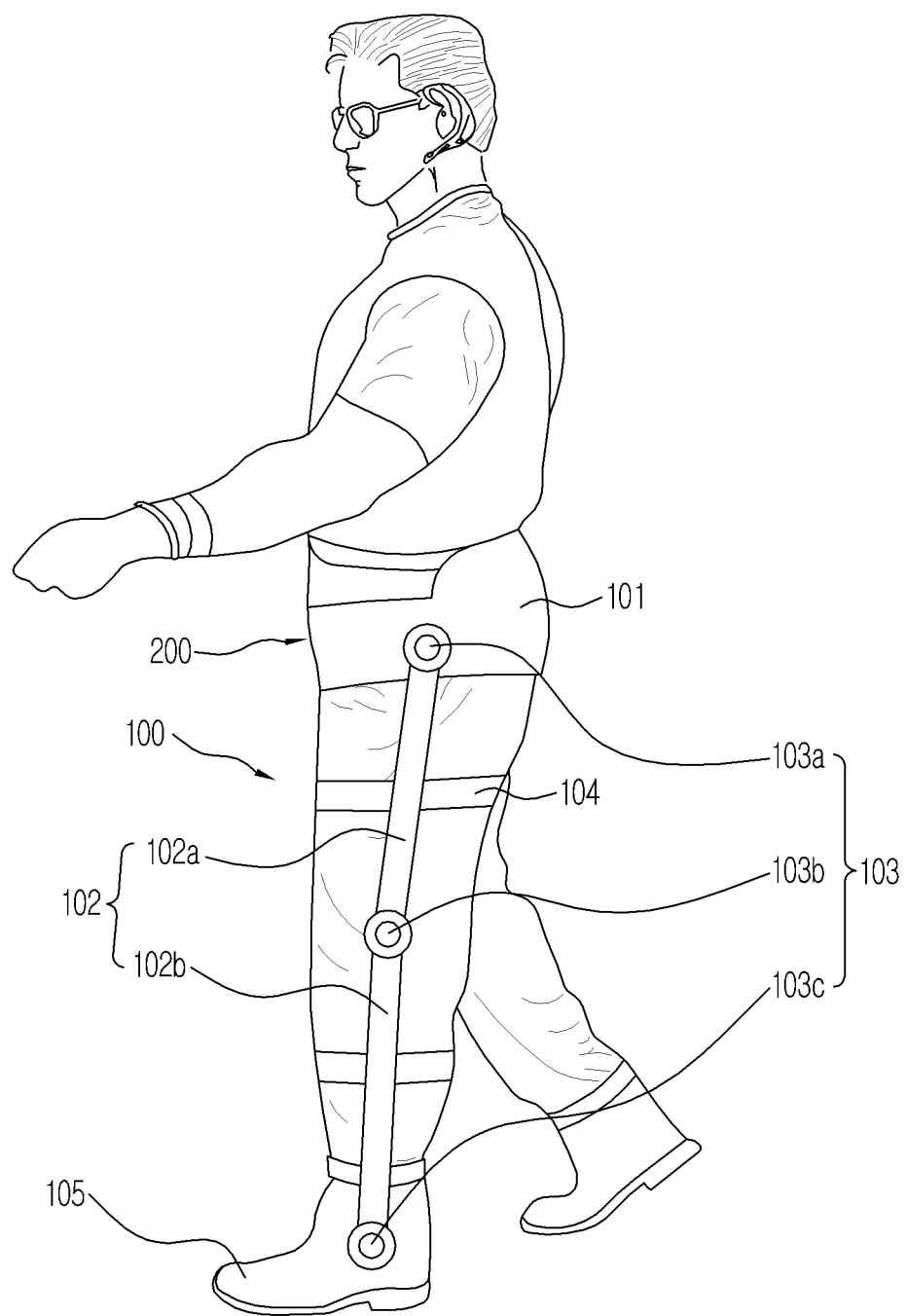
FIG. 1 illustrates an exterior of a wearable robot in accordance with some example embodiments.

Purposes, particular advantages, and new features of the example embodiments will be more apparent from the following detailed description and exemplary embodiments associated with the attached drawings. When adding reference numerals to elements of the drawings in the specification, it should be noted that like reference numerals if possible are used for like elements even though like elements are shown in different drawings. Also, in the description of the example embodiments, if it is determined that a detailed description of commonly-used technologies or structures may unnecessarily obscure the subject matter of the example embodiments, the detailed description will be omitted. It will be understood that although the terms first and second are used herein to describe various elements, these elements should not be limited by these terms. These terms are only used to distinguish one element from another element.

Reference will now be made in detail to example embodiments, some examples of which are illustrated in the accompanying drawings, wherein like reference numerals refer to like elements throughout.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Although a walking assisting robot among types of wearable robots will be described in the example embodiments, the example embodiments apply to not only the walking assisting robot but also all types of wearable robots that assist a wearer's muscle strength.

FIG. 1 illustrates an exterior of the walking assisting robot in accordance with some example embodiments.

Referring to FIG. 1, a walking assisting robot may include a robot unit (assistance device) 100 and a controller 200.

The robot unit 100 is configured as an instrument for assisting a wearer's walking and may include parts, such as joints and a motor for a walking movement, an actuator, such as a hydraulic and pneumatic cylinder, and a belt used to be united with the wearer's legs. The robot unit 100 may assist the wearer's walking movement by operating the joints and the actuator under the control of the controller 200.

The robot unit 100 may include a waist wearing portion 101, a support portion 102, a joint portion 103, and a fixing portion 104.

The waist wearing portion 101 may be worn on a wearer's waist and may be designed and/or adjusted according to a shape or a size of the wearer's waist part. Thus, the waist wearing portion 101 may stably support the waist of a body without any deformation according to the wearer's body type.

Although not specifically shown in FIG. 1, the waist wearing portion 101 may include a waist support fixture (not shown) that is placed at a rear side of the wearer's waist and stably supports the wearer's waist, and a band portion (not shown) that is formed to surround the wearer's abdominal part such that a burden of load applied to the wearer's waist may be reduced.

The controller 200 may be installed at the waist wearing portion 101. However, example embodiments are not limited thereto.

The support portion 102 may support a wearer's legs. As illustrated in FIG. 1, the support portion 102 may include a first support frame 102a and a second support frame 102b having desired (or, alternatively, predetermined) lengths.

The first support frame 102a and the second support frame 102b may be bars disposed on a plate. However, example embodiments are not limited thereto.

The first support frame 102a may be placed at an upper part of a wearer's knee, and one end of the first support frame 102a may be connected to the above-described waist wearing portion 101, and the other end of the first support frame 102a may be connected to the second support frame 102b. The second support frame 102b may be placed at a lower part of the wearer's knee, and one end of the second support frame 102b may be connected to the first support frame 102a, and the other end of the second support frame 102b may be connected to a shoe portion 105.

A portion in which one end of the first support frame 102a is connected to the waist wearing portion 101, a portion in which the other end of the first support frame 102a is connected to one end of the second support frame 102b, and a portion in which the other end of the second support frame 102b is connected to the shoe portion 105, may be rotatably connected to one another. However, example embodiments are not limited thereto.

Also, each connection portion may have at least 1 degree of freedom (DOF). However, example embodiments are not limited thereto. A degree of freedom (DOF) is a DOF at forward kinematics or inverse kinematics. A DOF of kinematics means the number of independent movements of an instrument or the number of variables used to determine independent movements of the instrument in relative positions between links. For example, an object in a three-dimensional space including an x-axis, a y-axis and a z-axis has one or more DOFs between 3 DOFs (position at each axis) for determining a spatial position of the object and 3 DOFs (rotation angle with respect to each axis) for determining a spatial orientation of the object. In detail, if the object is movable along each of the three axes and is rotatable around each axis, the object will be understood to have 6 DOFs.

Also, the first support frame 102a and the second support frame 102b may be adjusted to have lengths corresponding to lengths of a wearer's legs.

The joint portion 103 may include a first joint portion 103a, a second joint portion 103b, and a third joint portion 103c. However, example embodiments are not limited thereto.

The first joint portion 103a is disposed in the portion in which one end of the first support frame 102a is connected to the waist wearing portion 101 and may assist with bending between the hips and thighs, and the second joint portion 103b is disposed in the portion in which the other end of the first support frame 102a is connected to one end of the second support frame 102b and may assist with bending of the knees, and the third joint portion 103c is disposed in the portion in which the other end of the second support frame 102b is connected to the shoe portion 105 and may assist with bending of the ankles.

Figure 2:
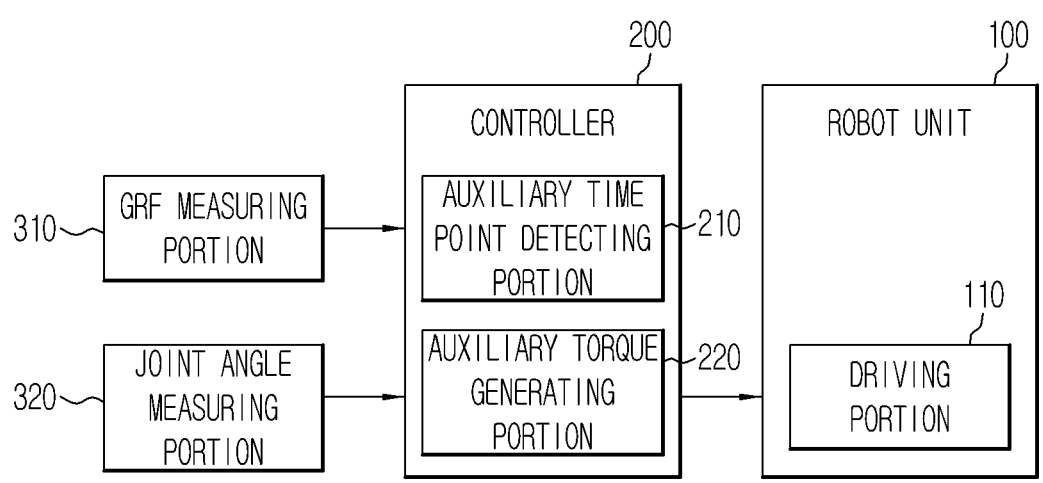
FIG. 2 is a block diagram illustrating a configuration of a wearable robot illustrated in FIG. 1.

FIG. 2 is a block diagram illustrating a configuration of a wearable robot illustrated in FIG. 1.

Referring to FIGS. 1 and 2, a driving portion may be disposed at each of the first joint portion 103a and the second joint portion 103b.

The driving portion 110 may transfer a driving force for a rotational movement to each of the first joint portion 103a and the second joint portion 103b.

For example, the driving portion 110 may include a pair of gears (not shown) disposed at each connection part and a driving motor (not shown) that is connected to a shaft of one of the pair of gears and is driven in response to electrical signals received from the controller 200. However, example embodiments are not limited thereto, for example, the driving portion 110 may be implemented using pneumatic and hydraulic methods (not shown) instead of the driving motor may also be used.

Due to the driving force transferred from the driving portion 110, the first support frame 102a and the second support frame 102b may bend, facilitating bending between the hips and thighs, and the knees and ankles.

A joint angle measuring portion 320 may be disposed at each of the first joint portion 103a and the second joint portion 103b to detect a joint angle associated therewith. For example, the joint angle measuring portion 320 may be disposed at the driving motor (not shown) of the driving portion 110 associated with each of the joint portions 103a and 103b. However, example embodiments are not limited thereto. Further, an encoder or a potentiometer may be used as the joint angle measuring portion 320. However, example embodiments are not limited thereto.

The fixing portion 104 is used to fix the first support frame 102a and the second support frame 102b to a wearer's lower legs and may be implemented as bands or belts. However, example embodiments are not limited thereto. Using the fixing portion 104, the first support frame 102a and the second support frame 102b are fixed to upper and lower parts of knees so that the moving first support frame 102a and the second support frame 102b can stably assist muscle strengths of the wearer's lower legs.

The robot unit 100 may further include a power portion (not shown) for providing power. The power portion (not shown) may be a battery. However, example embodiments are not limited thereto.

The robot unit 100 may further include the shoe portion 105. The shoe portion 105 may surround a wearer's feet. Further, as discussed in more detail below, the shoe portion 105 may assist in determining the wearer's walking state.

The shoe portion 105 may further include a fastening unit (not shown), such as a fabric hook and loop fastener or a snap, which is disposed at an upper part of the shoe portion 105 to allow the wearer to remove off the shoe portion 105 from their feet. However, example embodiments are not limited thereto, for example, the shoe portion 105 may include various types of one touch type fixing structures to attach the shoe portion 105 to the feet of the wearer.

In detail, the shoe portion 105 is used to surround and protect the wearer's feet and to measure the wearer's walking state. Sides of the shoe portion 105 may be rotatably coupled to the other end of the second support frame 102b.

Also, an upper part of the shoe portion 105 coupled to the second support frame 102b is connected to the driving motor (not shown) of the driving portion 110 for the second joint portion 103b using a wire so that a bending angle of ankles can be determined according to an angle converted by driving of the driving motor (not shown).

The shoe portion 105 assists the controller 200 in determining the wearer's left and right walking operations based on a pressure value measured by a ground reaction force (GRF) measuring portion 310, thereby measuring the wearer's walking state, simultaneously adjusting the bending angle of ankles using the wire when the shoe portion 105 varies according to driving of the driving motor (not shown), and enabling the wearer to stably walk.

The GRF measuring portion 310 may be used to measure a GRF exerted by the ground on a wearer's soles in contact therewith. Here, the GRF is a force exerted by the ground on a body in contact with it, the GRF having the same size as and an opposite direction to gravity or an internal force within the body when the gravity or the internal force within the body exerts on the ground. That is, the GRF is a force at which the wearer steps on the ground.

The GRF measuring portion 310 is used to measure a GRF exerted by the ground on the wearer's soles in contact with therewith, as described above. The GRF measuring portion 310 may be disposed on a bottom surface of the shoe portion 105 that corresponds to the wearer's soles. However, example embodiments are not limited thereto.

A force sensing resister (FSR) sensor or a pressure sensor may be used as the GRF measuring portion 310. However, example embodiments are not limited thereto. Also, a plurality of GRF measuring portions 310 may be disposed on the bottom surface of the shoe portion 105, but example embodiments are not limited thereto.

AS discussed in more detail with reference to FIGS. 3 to 5, the controller 200 may include an auxiliary time point detecting portion 210 and an auxiliary torque generating portion 220. However, example embodiments are not limited thereto.

Figure 3:
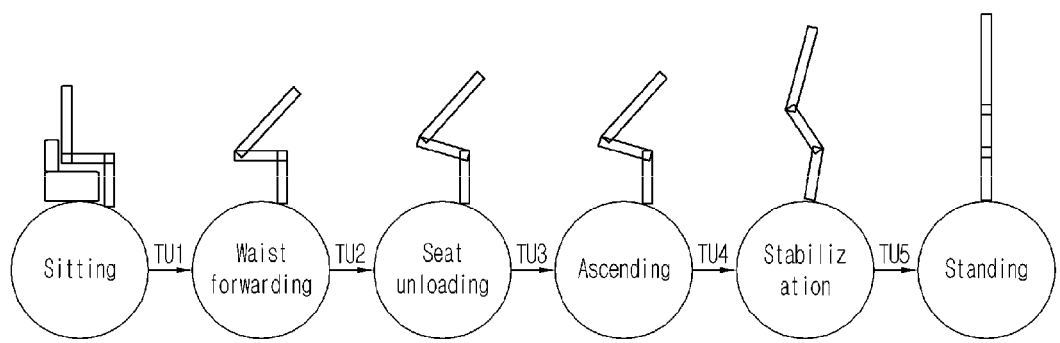
FIG. 3 is a conceptual view sequentially illustrating a wearer's standing movement.
Figure 4:
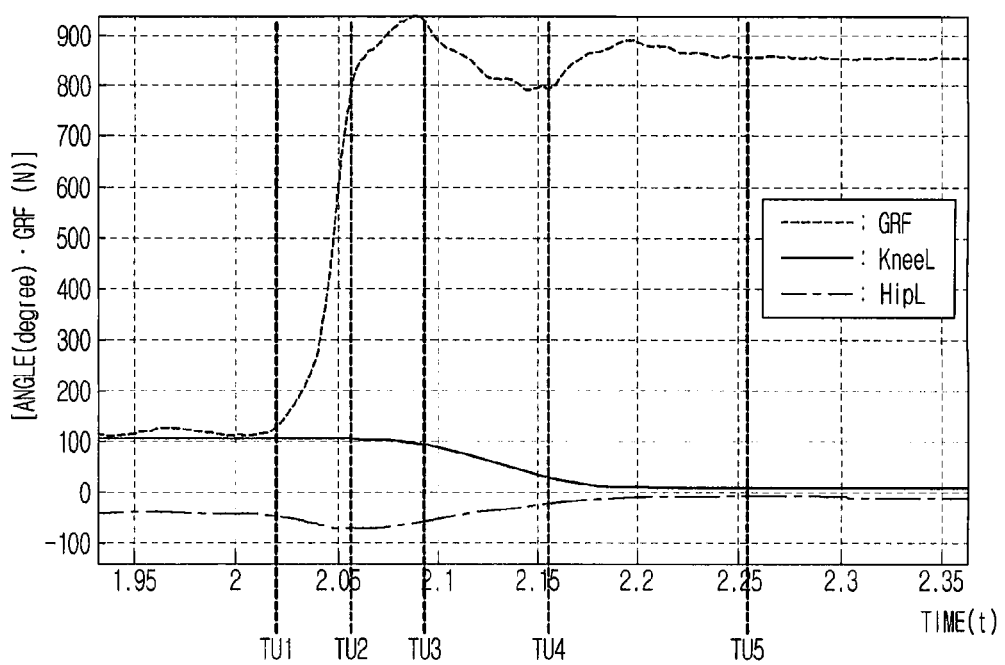
FIG. 4 is a graph showing a ground reaction force (GRF) and a joint angle between hips and knees in operations of the standing movement.
Figure 5:
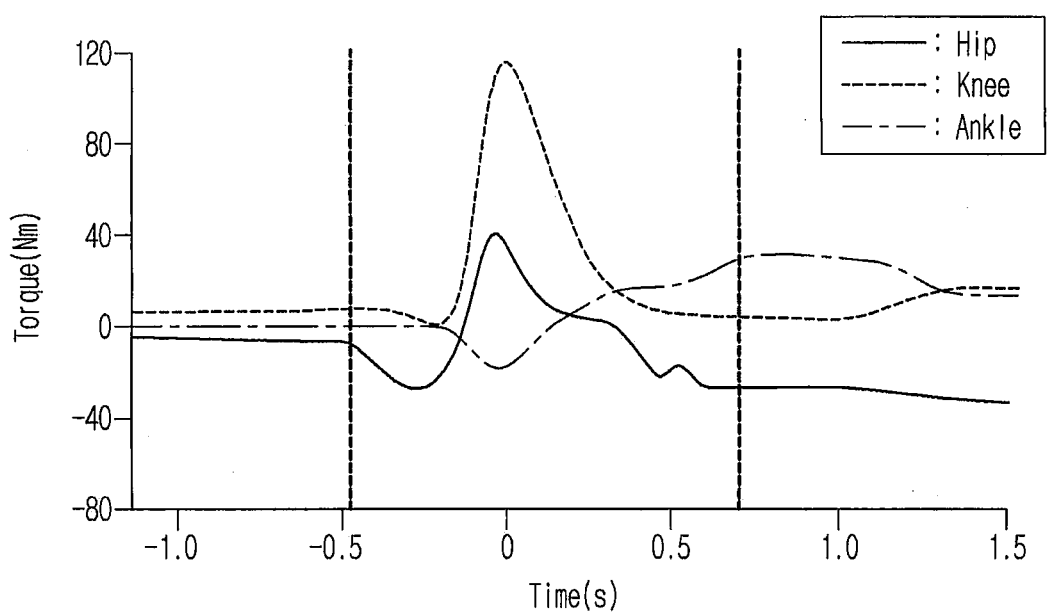
FIG. 5 is a graph showing load torques applied to hips, knees, and ankles, respectively, in operations of the standing movement.

FIG. 3 is a conceptual view sequentially illustrating a wearer's standing movement, FIG. 4 is a graph showing a ground reaction force (GRF) and joint angles of hips and knees in operations of the standing movement, and FIG. 5 is a graph showing load torques applied to a hip joint, a knee joint, and an ankle joint, respectively, in operations of the standing movement.

Referring to FIGS. 3 to 5, as a user stands from a sitting state, the wearer bends the waist forward, unloads a seat, ascends, stabilizes, and then fully stands.

In this case, an operation in which the wearer bends the waist forward in the sitting state, is referred to as TU1, an operation in which the wearer unloads the seat in the waist forwarding state, is referred to as TU2, an operation in which the wearer lifts the body in the seat unloading state, is referred to as TU3, an operation in which the wearer stabilizes in the ascending state, is referred to as TU4, and an operation in which the wearer fully stands in the stabilization state, is referred to as TU5.

Referring to FIG. 4, when operations TU1 to TU2 are performed, the GRF may increase rapidly. Also, referring to FIG. 5, in TU2 (Times(s)=0) in which the wearer unloads the seat in the waist forwarding state, a largest load torque may be applied to the hip joint, the knee joint, and the ankle joint.

Thus, by detecting a time point immediately before the seat unloading operation TU2 among the above-described operations, a spare time for accelerating the driving motor can be obtained so as to increase the load torque applied to the hip joint, the knee joint, and the ankle joint so that the wearer's resistance caused by rapid acceleration or deceleration can be reduced and a torque in a softer form can be generated.

To predict the seat uploading operation TU2, a wearer's standing intention may be detected before there is a change in the joint angle of the hip joint and the joint angle of the knee joint. To detect the upcoming occurrence of operation TU2, a time point at which a time variation rate of the GRF and the joint angle of the knee joint cross each other is detected, and the time point is determined as a time point at which the wearer starts the standing movement. This will be described in detail below.

The GRF measuring portion 310 disposed on the bottom surface of the shoe portion 105 corresponding to the wearer's soles, may be used to measure a GRF exerted by the ground on the wearer's soles in contact therewith.

Thus, the GRF measuring portion 310 may detect a time point at which the seat is unloaded so that the wearer can stand, i.e., a time point at which the GRF increases rapidly. The GRF measured by the GRF measuring portion 310 may be provided to the controller 200.

The joint angle measuring portion 320 is disposed at the first joint portion 103a and the second joint portion 103b of the robot unit 100 and is used to measure a hip joint angle and a knee joint angle, as described above. The hip joint angle and the knee joint angle measured by the joint angle measuring portion 320 may be provided to the controller 200 that will be described later.

The controller 200 may be used to control an overall operation of the walking assisting robot. The controller 200 may detect a time point at which the wearer starts to stand, using the GRF measured by the GRF measuring portion 310 and the knee joint angle measured by the joint angle measuring portion 320 and may provide control signals for generating the auxiliary torque to the robot unit 100.

In detail, the controller 200 may detect a time point at which a time variation rate (a differential value) of the GRF and the knee joint angle cross each other, may determine the detected crossing time point as a time point at which the wearer starts to stand, and may provide control signals for generating the auxiliary torque to the driving portion 110 of the robot unit 100. The control signals generated by the controller 200 may be as electrical signals for driving the driving motor of the driving portion 110.

The auxiliary time point detecting portion 210 calculates the time variation rate (the differential value) of the GRF provided from the GRF measuring portion 310 and detects a time point at which the calculated time variation rate of the GRF crosses the knee joint angle provided from the joint angle measuring portion 320, from a section in which the time variation rate of the GRF increases.

Figure 7:
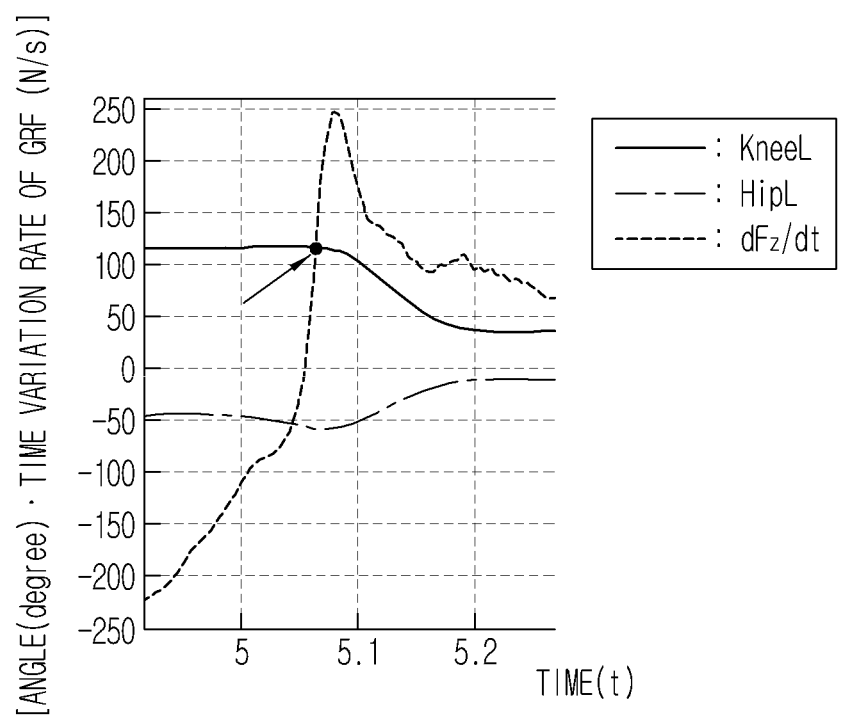
FIG. 7 is a graph showing time points at which an increasing GRF and a knee joint angle cross each other, while the wearer makes a standing movement.

FIG. 7 is a graph showing time points at which an increasing GRF and a knee joint angle cross each other, while the wearer makes a standing movement.

Referring to FIGS. 2, and 7, the auxiliary time point detecting portion 210 may detect a portion in which a graph showing the calculated time variation rate of the GRF and a graph showing the knee joint angle provided from the joint angle measuring portion 320 overlap each other on one graph and cross each other.

This can be represented by the following Equation 1. That is, the auxiliary time point detecting portion 210 may detect a time point at which two conditions of the following Equation 1 are satisfied.

$$\frac{dF_z}{dt} = \theta_{knee} \text{ and } \frac{dF_z}{dt} > 0, \text{ where } \frac{dF_z}{dt}$$  [Equation 1]

may be a time variation rate [Newton/second] of the GRF, and $\theta_{knee}$ may be a knee joint angle (degree). That is, a time at which the time variation rate of the GRF is 0 or more and simultaneously the GRF reaches the knee joint angle, is detected.

As illustrated in FIG. 7, when the calculated time variation rate (differential value) of the GRF, the hip joint angle and the knee joint angle provided from the joint angle measuring portion 320 are indicated on the same graph, a time point at which the increasing GRF and the knee joint angle cross each other, as a portion indicated by an arrow, can be detected.

In this way, since the crossing time point between the time variation rate of the GRF and the knee joint angle is detected, a time point at which the wearer starts to stand, can be uniformly detected either when the wearer's standing speeds are different or when the wearer's standing postures are different.

Figure 8:
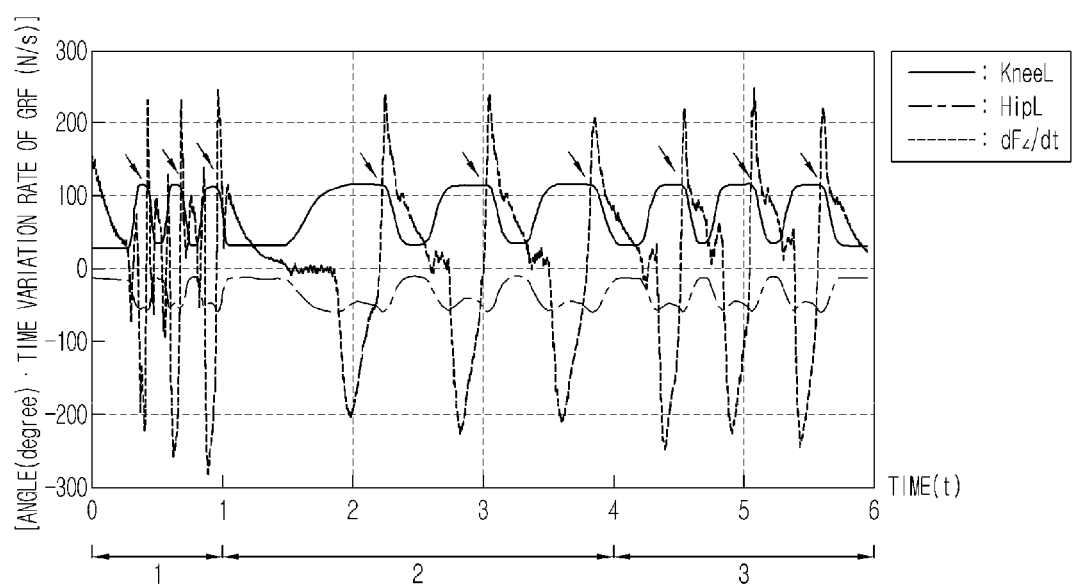
FIG. 8 is a graph showing crossing time points detected according to standing movement speeds.

FIG. 8 is a graph showing crossing time points detected according to standing movement speeds.

Referring to FIG. 8, a crossing time point like a portion indicated by an arrow can be detected in any case, T0 to T1, the wearer stands at a high speed (1), a case, T2 to T4, that the wearer stands at a low speed (2), and a case, T4 to T6, that the wearer stands at a middle speed (3).

Figure 9:
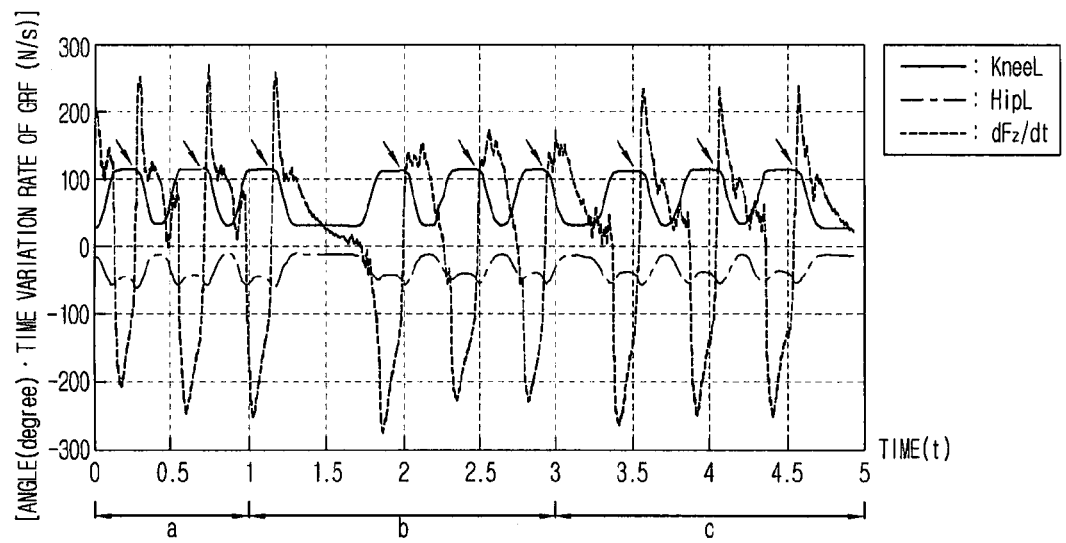
FIG. 9 is a graph showing crossing time points detected according to standing postures.

FIG. 9 is a graph showing crossing time points detected according to standing postures.

Also, as illustrated in FIG. 9, crossing time, indicated by arrows, can be detected in any case among a case that the wearer stands with his/her arms folded (a), a case that the wearer stands by placing his/her hand on an armrest (b), and a case that the wearer stands by placing his/her hand on the knee (c).

When the GRF provided from the GRF measuring portion 310 has a small value in which the GRF cannot meet the knee joint angle, the auxiliary time point detecting portion 210 may normalize the provided GRF and may detect a time point at which the normalized GRF and the knee joint angle cross each other. The GRF provided from the GRF measuring portion 310 may be normalized using the following Equation 2.

$$F_{znorm} = k \frac{F_z}{|F_{zmax}|},$$ [Equation 2]

where $F_z$ is a measured GRF, $F_{znorm}$ is a normalized GRF, $F_{zmax}$ is a maximum value of the measured GRF, and k is a proportional constant.

That is, the auxiliary time point detecting portion 210 may normalize the measured GRF by multiplying a value obtained by dividing all measured GRFs by an absolute value of the maximum value among the measured GRFs by a desired (or, alternatively, a predetermined) proportional constant and may detect a time point at which the GRF crosses the knee joint angle using the time variation rate (differential value) of the normalized GRF.

The auxiliary torque generating portion 220 is used to generate an auxiliary torque to be applied to the wearable robot from an auxiliary time point detected using the above-described auxiliary time point detecting portion 210, i.e., from a time point at which the time variation rate of the GRF crosses the knee joint angle.

The auxiliary torque generating portion 220 may generate an auxiliary torque having a wave shape in which the wearer does not feel resistance. In detail, the auxiliary torque generating portion 220 may generate an auxiliary torque using the following Equation 3.

$$\tau_{assist} = \sum_{i=1}^{n} A_i \sin(\omega_i t + \phi_i),$$ [Equation 3]

where $\tau_{assist}$ is an auxiliary torque, $A_i$ is the size of an i-th sinusoidal wave, $\omega_i$ is a frequency of the i-th sinusoidal wave, t is time, and $\phi_i$ is a phase of the i-th sinusoidal wave.

That is, the auxiliary torque generating portion 220 may generate control signals that instruct the driving portions 110 of the robot 100 to generate an auxiliary torque, where the auxiliary torque is shaped to have a soft shape, such as a trigonometrical function wave shape, by overlapping several sinusoidal waves having different frequencies, phases, and sizes. Therefore, under the control of the controller 200, the driving motors generate an auxiliary torque that does not increase or decrease rapidly so that the wearer does not feel repulsion or resistance.

Figure 10:
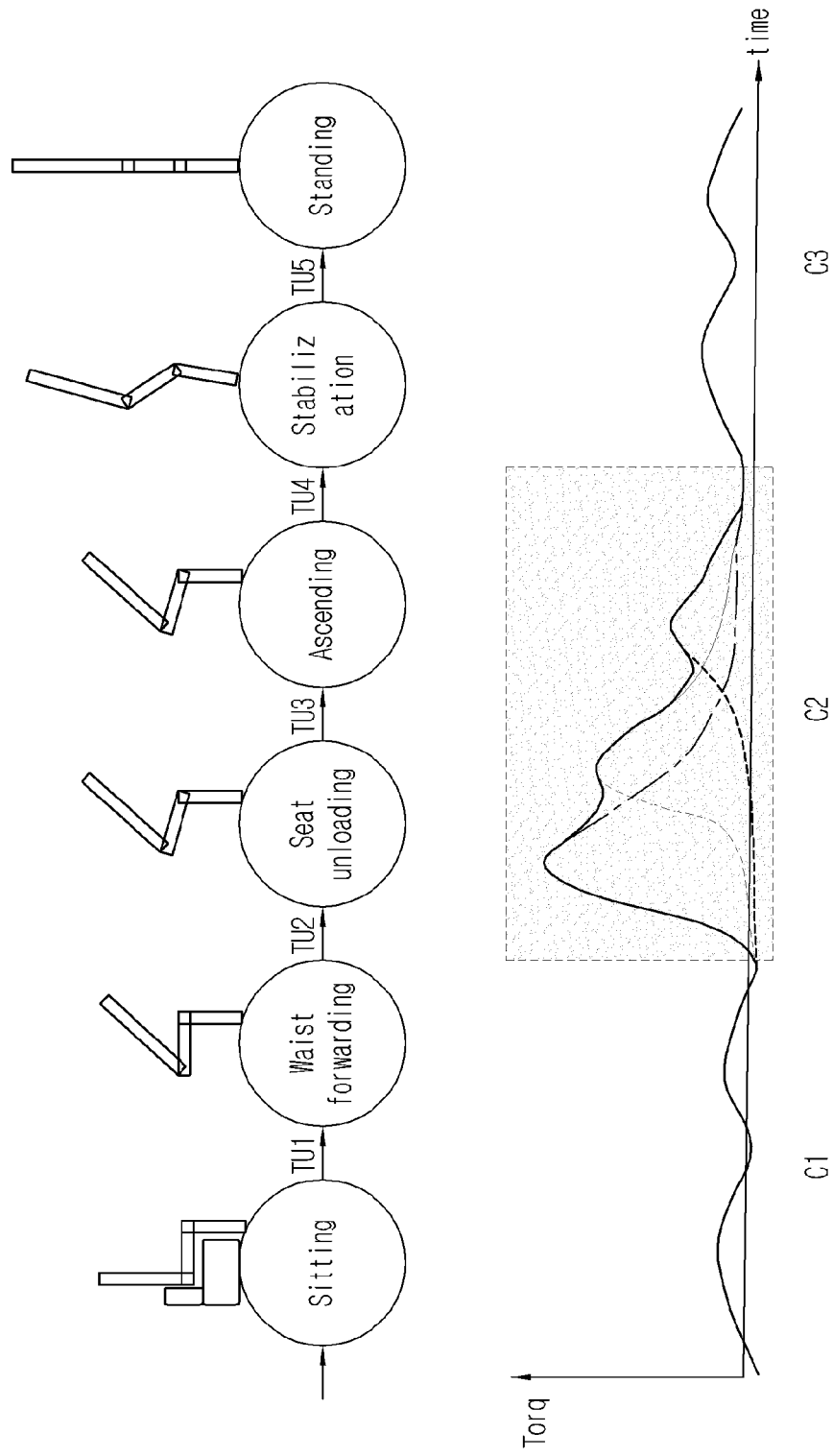
FIG. 10 is a conceptual view illustrating applying time points, applying times, and shapes of auxiliary torques.

FIG. 10 is a graph showing auxiliary torque applying time points and shapes.

Referring to FIG. 10, the auxiliary torque having an overlapping trigonometrical function wave shape, like a portion C2 is generated and is applied to the wearable robot before (e.g. immediately before) a time point T2 at which a seat unloading operation starts up to a stabilization time point T5 so that the wearer may not feel inconveniences caused by the generated auxiliary torque.

Although FIG. 10 illustrates a case that the auxiliary torque is shaped similar to a shape of a pulse wave, the shape of the generated auxiliary torque is not limited thereto.

Also, the controller 200 may output a target torque obtained by adding a frictional force compensation torque and a dynamics compensation torque to the auxiliary torque generated using the auxiliary torque generating portion 220. However, example embodiments are not limited thereto. This can be represented by the following Equation 4.

$$\tau_{desired} = \tau_{friction} + \tau_{dyn} + \tau_{assist}$$ [Equation 4]

where $\tau_{desired}$ is a target torque, $\tau_{friction}$ is a frictional force compensation torque, and $\tau_{dyn}$ is a dynamics compensation torque.

As shown in Equation 4, the controller 200 may instruct the robot unit 100 to generate a final target torque that includes a frictional force compensation torque $\tau_{friction}$, a dynamics compensation torque $\tau_{dyn}$, and the auxiliary torque $\tau_{assist}$ generated by the auxiliary torque generating portion 220. However, example embodiments of are not limited thereto.

Also, the controller 200 may determine a time when the above-described auxiliary torque $\tau_{assist}$ is applied to the wearable robot 100.

In detail, the controller 200 may measure speed for waist forwarding so that the wearer can stand and may determine the time when the auxiliary torque is applied to the wearable robot, using the speed.

In this case, the controller 200 may measure the speed for waist forwarding by differentiating the hip joint angle measured by the joint angle measuring portion 320. However, example embodiments are not limited thereto. Also, the auxiliary torque applying time according to measured speeds may be determined using data from a database. However, example embodiments are not limited thereto.

That is, the controller 200 may measure the hip joint angle when the wearer makes a waist forwarding movement using the joint angle measuring portion 320, as described above, may calculate speed at which the wearer makes the waist forwarding movement by differentiating the measured hip joint angle, and then may determine an auxiliary torque applying time corresponding to the calculated speed using information stored in the database. The auxiliary torque can be applied to the robot unit 100 for the determined auxiliary torque applying time.

Also, although not shown in FIG. 2, the walking assisting robot in accordance with the current embodiment may further include a mode conversion portion (not shown).

The mode conversion portion (not shown) may be used to select a walking mode, a posture mode, and walking speed. In detail, the mode conversion portion (not shown) may include a walking mode conversion portion (not shown) that can select a walking mode for a flat road, a rough road, and stairs, a posture mode conversion portion (not shown) that can select postures for sitting, standing, and an inclined surface, and a walking speed conversion portion (not shown) that can select walking speed, such as fast, slow, and normal. However, example embodiments are not limited thereto.

As described above, the walking assisting robot in accordance with the current embodiment measures the GRF with respect to the wearer's soles and the knee angle, detects a crossing time point thereof, and determines the detected crossing time point as an auxiliary torque applying time point so that an appropriate auxiliary torque applying time point can be detected regardless of a movement speed according to wearers, postures, and the usage of an auxiliary instrument.

Also, the walking assistance robot can determine a time when the auxiliary torque is applied based on the standing movement speed, and the auxiliary torque may be shaped to have a gentle slope such that the auxiliary torque does not increase or decrease rapidly. Therefore, the wearer's resistance or repulsion caused by the auxiliary torque may be reduced.

Hereinafter, various example embodiments of methods of controlling the walking assisting robot will be described.

Figure 6:
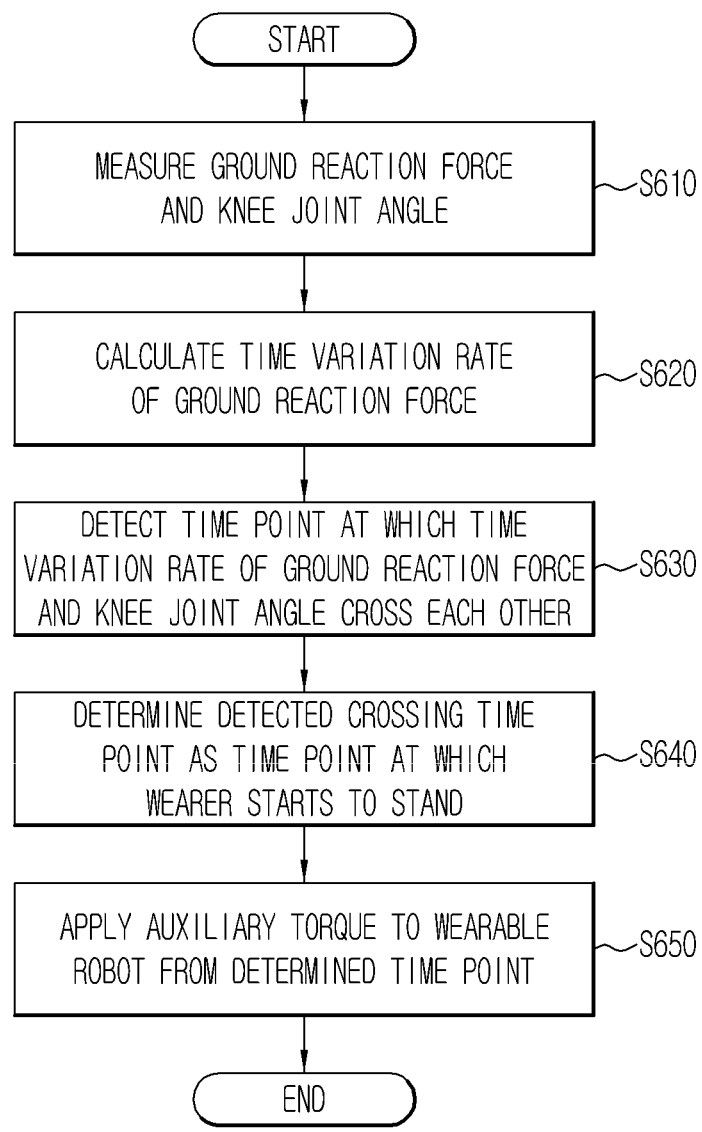
FIG. 6 is a flowchart illustrating a method of controlling a wearable robot in accordance with some example embodiment.

FIG. 6 is a flowchart illustrating a method of controlling a wearable robot in accordance with some example embodiments.

Referring to FIG. 6, a method of controlling the wearable robot may include measuring, using the GRF measuring portion 310, a GRF exerted by the ground on a wearer's soles in contact with them and the wearer's knee joint angle (S610). The GRF means a force exerted by the ground on a body in contact with it, the GRF having the same size as and an opposite direction to gravity or an internal force within the body when the gravity or the internal force within the body exerts on the ground. The GRF may be a force at which the wearer steps on the ground.

Also, in the current embodiment, the controller 200 may measure the wearer's knee joint angle using the joint angle measuring portion 320 disposed at, for example, the second joint portion 103*b*. However, example embodiments are not limited thereto, for example, the joint angle measuring portion 320 may be disposed in the driving motor (not shown) of the driving portion 110.

In operation S620, the controller 200 (e.g., the auxiliary time point detecting portion 210) may calculate a time variation rate of the GRF measured in Operation S610. The time variation ratio of the GRF may be a differential value obtained by differentiating the GRF.

Although not shown in FIG. 6, the method of controlling the wearable robot may further include normalizing the measured GRF before calculating the time variation rate of the GRF. The controller 200 may normalize the measured GRF, using Equation 2, when the measured GRF is smaller than a desired (or, alternatively, a predetermined) threshold value and cannot meet the knee joint angle.

In operation S630, the controller 200 (e.g. the auxiliary time point detecting portion 210) may detect a time point at which the graph of the time variation rate of the GRF calculated in Operation S620 and the graph of the knee joint angle measured in Operation S610 cross each other.

In detail, the controller 200 may detect the crossing time point between the time variation rate of the GRF and the knee joint angle by detecting a time point at which the calculated time variation rate of the GRF crosses the knee joint angle provided from the joint angle measuring portion 320, from a section in which the calculated time variation rate of the GRF increases.

For example, as illustrated in FIG. 7, the controller 200 may detect the crossing time point between the time variation rate of the GRF and the knee joint angle by indicating the graph of the calculated time variation rate of the GRF and the graph of the measured knee joint angle on one graph and then by detecting a crossing time point thereof. The controller 200 may detect this crossing time point as a point in time at which two conditions of Equation 1 are satisfied.

In operation S640, the controller 200 may determine the detected crossing time point as a time point at which the wearer starts to stand. Also, the auxiliary time point detecting portion 210 may determine that the auxiliary torque is applied to the wearable robot from the detected time point.

In operation S650, an auxiliary torque is generated, and the generated auxiliary torque is applied to the wearable robot from the time point determined in Operation S640.

The auxiliary torque may be generated to have a trigonometrical function wave shape in which a plurality of sinusoidal waves having different frequencies, sizes, and phases overlap each other, as illustrated in FIG. 10. The auxiliary torque having the trigonometrical function wave shape in which the plurality of sinusoidal waves overlap each other, may be generated using the above-described Equation 3. Driving of the driving motor is controlled to output the auxiliary torque having the trigonometrical function wave shape in which the plurality of sinusoidal waves overlap each other, so that the auxiliary torque generated by driving of the driving motor does not increase or decrease rapidly and the wearer does not feel repulsion or resistance with respect to the auxiliary torque.

Although not shown in FIG. 6, the method of controlling the wearable robot may further include determining a time when the auxiliary torque is applied to the wearable robot.

In detail, the controller 200 may measure speed of waist forwarding so that the wearer can stand and may determine the time when the auxiliary torque is applied to the wearable robot, using the speed of waist forwarding. That is, the speed of waist forwarding is measured so that wearer's standing speed can be predicted and the auxiliary torque can be applied to the wearable robot for a time corresponding to the predicted speed.

In this case, the controller 200 may measure the speed of waist forwarding by differentiating the hip joint angle measured by the joint angle measuring portion 320. However, example embodiments are not limited thereto. Also, the time when the auxiliary torque is applied to the wearable robot according to measured speeds may be determined using a database. However, example embodiments are not limited thereto.

That is, the controller 200 may measure the hip joint angle when the wearer makes a waist forwarding movement using the joint angle measuring portion 320, as described above, may calculate speed at which the wearer makes the waist forwarding movement by differentiating the measured hip joint angle, and then may determine an auxiliary torque applying time corresponding to the calculated speed using information stored in the database. The auxiliary torque can be applied to the robot unit 100 for the determined auxiliary torque applying time.

In the above-described embodiments, elements of the wearable robot may be implemented with a 'module'. Here, the 'module' means a software element or a hardware element, such as a field programmable gate array (FPGA) or an application specific integrated circuit (ASIC), and the module may perform functions. However, the module is not limited to software or hardware. The module may be configured to be in a storage medium that may address the module or to execute one or more processors.

As an example, the module may include elements, such as software elements, object-oriented software elements, class elements, and task elements, processes, functions, properties, procedures, subroutines, segments for a program code, drivers, firmware, micro-codes, circuits, data, databases, data structures, tables, arrays, and variables. Functions provided by elements and modules may be combined with a smaller number of elements and modules or may be subdivided into additional elements and modules. Furthermore, the elements and modules may execute one or more central processing units (CPUs) within a device.

Some embodiments may be embodied through a medium including a computer-readable code/command for controlling at least one processing element of the above-described embodiments, for example, a non-transitory computer-readable medium. The medium may correspond to a medium that enables storage and/or transmission of the computer-readable code.

The processing element may include a processor or a computer processor, and the processing element may be distributed and/or included in one device. In more detail, the controller 200 may include a processor and a memory (not shown).

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform the operations illustrated in FIG. 6, such that the controller 200 controls the driving portions 110 of the robot unit 100 based on signals from the GRF measuring portion 310 and the joint angle measuring portion 320.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

Although a few example embodiments have been shown and described, it would be appreciated by those skilled in the art that changes may be made in these embodiments without departing from the principles and spirit thereof, the scope of which is defined in the claims and their equivalents.

What is claimed is:

1. A method of controlling a wearable robot configured to be worn by a user, the method comprising:
   measuring a ground reaction force (GRF) and a knee joint angle, the GRF being a force exerted on at least one sole of the user and the knee joint angle being an angle of one or more knee joints of the user;
   plotting a time variation rate of the GRF on a first graph;
   plotting the knee joint angle on a second graph;
   overlaying the second graph on the first graph to generate a third graph;
   detecting a point in time at which a time variation rate of the GRF and the knee joint angle cross each other on the third graph;
   determining the detected point in time as a point in time at which the user has begun standing; and applying, via an actuator, an auxiliary torque to the wearable robot from the determined point in time.

2. The method of claim 1, further comprising:
   generating the auxiliary torque, after the step of determining that the user has begun standing.

3. The method of claim 2, wherein the step of generating the auxiliary torque generates the auxiliary torque having a trigonometrical function wave shape in which a plurality of sinusoidal waves overlap each other.

4. The method of claim 3, wherein the plurality of sinusoidal waves have different frequencies, sizes, and phases.

5. The method of claim 2, wherein the step of generating the auxiliary torque further comprises:
   determining a time when the generated auxiliary torque is applied to the wearable robot.

6. The method of claim 5, wherein the determining a time when the generated auxiliary torque is applied to the wearable robot comprises:
   measuring a hip joint angle when the user leans forward at a movement speed;
   calculating the movement speed by differentiating the measured hip joint angle; and
   determining the auxiliary torque applying time based on the movement speed.

7. The method of claim 1, further comprising:
   normalizing the measured GRF using the following Expression 1, if the measured GRF is smaller than a threshold value;

$$F_{znorm} = k\frac{F_z}{|F_{zmax}|} \quad \text{Expression 1}$$

where $F_z$ is a measured GRF, $F_{znorm}$ is a normalized GRF, $F_{zmax}$ is a maximum value of the measured GRF, and k is a proportional constant.

8. A method of controlling a wearable robot configured to be worn by a user, the method comprising:
   measuring a ground reaction force (GRF) and a knee joint angle, the GRF being a force exerted on at least one sole of the user, and the knee joint angle being an angle of one or more knee joints of the user;
   plotting a time variation rate of the GRF on a first graph;
   plotting the knee joint angle on a second graph;
   overlaying the second graph on the first graph to generate a third graph;
   detecting a point in time at which a time variation rate of the GRF and the knee joint angle cross each other on the third graph;
   determining the detected point in time as a point in time at which the user has begun standing;
   generating an auxiliary torque having a trigonometrical function wave shape such that the auxiliary torque includes a plurality of overlapping sinusoidal waves; and
   applying, via an actuator, the generated auxiliary torque to the wearable robot from the determined point in time.

9. The method of claim 8, wherein the plurality of overlapping sinusoidal waves have different frequencies, sizes, and phases.

10. The method of claim 8, wherein the step of generating the auxiliary torque further comprises:
 determining a time when the generated auxiliary torque is applied to the wearable robot.

11. The method of claim 10, wherein the step of determining of the time when the generated auxiliary torque is applied to the wearable robot comprises:
 measuring a hip joint angle when the user leans forward at a movement speed;
 calculating the movement speed by differentiating the measured hip joint angle; and
 determining the auxiliary torque applying time based on the calculated movement speed.

12. A wearable robot configured to be worn by a user, the wearable robot comprising:
 an assistance device configured to assist muscles of the user;
 sensors configured to,
  measure a ground reaction force (GRF) exerted on at least one sole of the user, and
  measure a knee joint angle and a hip joint angle of the user, the knee joint angle being an angle of one or more knee joints of the user and the hip joint angle being an angle between a hip and at least one leg of the user; and
 a controller configured to,
  detect a point in time at which a time variation rate of the GRF and the knee joint angle cross each other when the time variation rate of the GRF and the knee joint angle are plotted by,
   plotting the time variation rate of the GRF on a first graph,
   plotting the knee joint angle on a second graph, and overlaying the second graph on the first graph to generate a third graph
  determine the detected point in time as a point in time at which the user has begun standing, and
  apply, via an actuator, an auxiliary torque to the assistance device from the determined point in time.

13. The wearable robot of claim 12, wherein the controller is configured to,
 generate the auxiliary torque having a trigonometrical function wave shape such that the auxiliary torque includes a plurality of overlapping sinusoidal waves, and
 apply the generated auxiliary torque to the assistance device when the controller determines that the user has begun standing.

14. The wearable robot of claim 12, wherein the controller is configured to,
 instruct the sensors to measure the hip joint angle of the user when the user leans forward at a movement speed,
 calculate the movement speed by differentiating the measured hip joint angle,
 determine a time when the auxiliary torque is applied to the assistance device based on the calculated movement speed, and
 apply the auxiliary torque to the assistance device for the determined time.

15. The wearable robot of claim 12, wherein, the controller is configured to normalize the measured GRF and calculate a time variation rate of the normalized GRF, if the measured GRF is smaller than a threshold value.

* * * * *